United States Patent
Buschke et al.

(10) Patent No.: US 7,210,329 B2
(45) Date of Patent: May 1, 2007

(54) METHOD FOR DETERMINING TEMPORAL AND AMPLITUDE THRESHOLD VALUES OF GATES DURING ULTRASOUND TESTING OF SPOT WELDING JOINTS

(75) Inventors: Paul Buschke, Hürth (DE); Bernd Kirchner, Erftstadt (DE)

(73) Assignee: Agfa NDT GmbH (DE)

( * ) Notice: Subject to any disclaimer, the term of this patent is extended or adjusted under 35 U.S.C. 154(b) by 131 days.

(21) Appl. No.: 10/512,806

(22) PCT Filed: May 13, 2003

(86) PCT No.: PCT/DE03/01545

§ 371 (c)(1),
(2), (4) Date: Apr. 15, 2005

(87) PCT Pub. No.: WO03/098207

PCT Pub. Date: Nov. 27, 2003

(65) Prior Publication Data

US 2005/0210953 A1  Sep. 29, 2005

(30) Foreign Application Priority Data

May 17, 2002 (DE) .............................. 102 22 600

(51) Int. Cl.
*G01N 29/30* (2006.01)
*G01N 29/28* (2006.01)
*G01N 29/38* (2006.01)
(52) U.S. Cl. ............................. 73/1.82; 73/597; 73/602; 73/609; 702/103; 702/116
(58) Field of Classification Search ................. 73/1.82, 73/597, 602, 609; 702/113, 116, FOR. 170
See application file for complete search history.

(56) References Cited

U.S. PATENT DOCUMENTS 3,554,029 A * 1/1971 Deininger, Jr. ............... 73/620

(Continued)

FOREIGN PATENT DOCUMENTS

JP  2000155112 A * 6/2000
SU  1430878 A * 10/1988

OTHER PUBLICATIONS

International Search Report; PCT/DE03/01545; Sep. 15, 2003 (date mailed).
Krautkraemer J. et al.; "State of the art in ultrasonic testing of sport welds"; XP-002206463; NDTnet Apr. 1998; vol. 3 No. 4 2 pages.

*Primary Examiner*—Thomas P. Noland
(74) *Attorney, Agent, or Firm*—Cantor Colburn LLP

(57) ABSTRACT

The invention relates to a method for determining the threshold value of screens which enable an evaluation of a sound coupling during the ultrasound testing of a series of spot welding joints of a selected type. Initially, a geometrical minimal thickness dMin is established for the spot welding joints. At least one echo of the front surface (entrance echo) is received in addition to one echo of the first reflection on a rear wall of the spot welding joint (first rear wall echo) and at least one further (n-th) rear wall echo. The propagation time tMin of the ultra sound pulse is defined for the path to the front surface to the rear wall and back to the front surface at a minimal thickness dMin and a propagation time tT for the total thickness. A first screen (B1) is set for the signal of the rear wall echo, starting at a moment in time t1S=tE+tMin−tSA and ending at a moment in time t1T=tE+tT+tSE, whereby tSA and tSE are additional small security measures. An n-th screen is correspondingly determined for the n-th rear wall echo. The testing head is oriented differently.

16 Claims, 2 Drawing Sheets

U.S. PATENT DOCUMENTS

Figure 1:
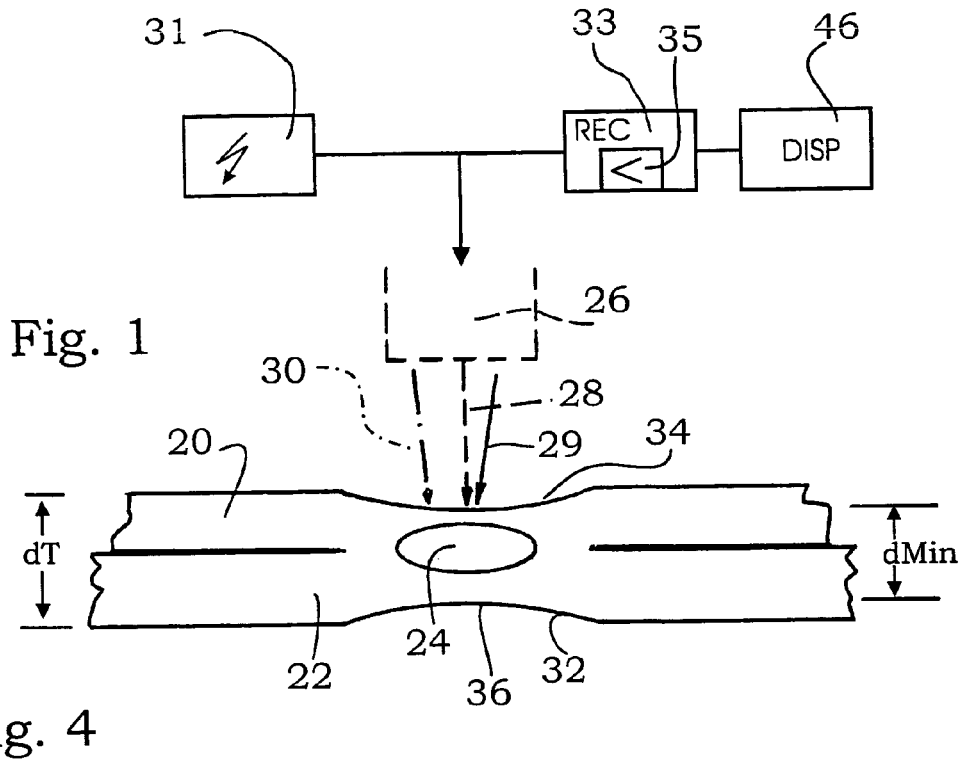

| | | | |
|---|---|---|---|
| 3,712,119 A | * 1/1973 | Cross et al. | 73/614 |
| 3,791,199 A | * 2/1974 | Toth et al. | 73/609 |
| 4,204,434 A | * 5/1980 | Whitsel | 73/622 |
| 4,208,917 A | 6/1980 | Aoyama et al. | 73/588 X |
| 4,265,119 A | 5/1981 | Dubertz et al. | 73/588 |
| 4,480,474 A | * 11/1984 | Kazama et al. | 73/600 |
| 5,063,779 A | * 11/1991 | Landry et al. | 73/622 |
| 5,085,082 A | * 2/1992 | Cantor et al. | 73/622 |
| 5,108,693 A | * 4/1992 | Landry et al. | 376/245 |
| 5,537,875 A | 7/1996 | Viehmann et al. | 73/588 |

* cited by examiner

METHOD FOR DETERMINING TEMPORAL AND AMPLITUDE THRESHOLD VALUES OF GATES DURING ULTRASOUND TESTING OF SPOT WELDING JOINTS

BACKGROUND OF THE INVENTION

The invention generally relates to a method for ultrasound testing of a series of spot welding joints of a selected type and is directed to improvement within such type testing methods, namely to determining threshold values for gates which permit to evaluate the quality of a sound coupling. The invention is primarily concerned with determining temporal threshold values and also proposes amplitude threshold values.

Methods for ultrasound testing of spot welding joints are well known, the reader being referred in this context to U.S. Pat. Nos. 4,208,917; 4,265,119 and 5,537,875.

The known methods may be divided into methods in which ultrasound testing is performed substantially concurrently with the making of the spot welding joints and into such methods by which an already made spot welding joint is tested subsequently by means of ultrasound. The invention only relates to the second type of method, meaning to subsequent testing.

The ultrasound testing of spot welding joints is based on the evaluation of the echo sequence of an ultrasound signal emitted into the spot welding joint, preferably of a pulse. Typically, a sequence of pulses is emitted. Heavily damped transmit/receive transducer probes or heads, which usually make use of film resonators and have a frequency typically ranging from 15 to 20 MHz, are utilized. The diameters of the transducers are approximately within the range of the diameter of the spot welding joints. Coupling typically occurs through a preliminary water stretch that is often sealed against the outside by a thin membrane. Direct contact of the water with the metal sheets is thus avoided.

Presently, ultrasound testing of spot welding joints is still mainly carried out by hand. Automation of testing is being strived for. The invention is intended to both simplify manual testing and to indicate ways for automatic testing.

BRIEF SUMMARY OF THE INVENTION

The invention indicates defined conditions permitting to evaluate the quality of coupling of an ultrasound probe to a concrete spot welding joint.

During practical testing, be it manually or mechanically performed, the probe is both displaced relative to the spot welding joint and oriented into different directions. The objective is to sufficiently register the welding spot achieved between neighboring individual metal sheets if the spot welding joint is good and to ultrasonically irradiate it. Optimum coupling is aimed at but must not necessarily be achieved, though. Good coupling means that the echo signals are clearly large enough to permit an evaluation, more specifically a digitization.

The invention provides a method of determining the threshold values of gates which enable an evaluation of a good sound coupling during the ultrasound testing of a series of spot welding joints of a selected type, with said spot welding joints being formed between at least a first metal sheet and a second metal sheet, the first metal sheet comprising a first sheet thickness and the second metal sheet a second sheet thickness, the method consisting in initially establishing a geometrical minimum thickness dMm of the spot welding joint, this minimum thickness being smaller than an overall sheet thickness dT of the metal sheets joined together by the spot welding joints, in coupling an ultrasound probe to a spot welding joint to be tested, in emitting at least one ultrasound pulse onto a front surface of the spot welding joint and receiving its echo signals, in receiving in addition to the echo signals at least one echo of the front surface (entrance echo), one echo of the first reflection on a rear wall of the spot welding joint (first rear wall echo) and at least one further ($n^{th}$) rear wall echo, in defining the propagation time tMin of the ultrasound pulse for the path from the front surface to the rear wall and back to the front surface at the minimum thickness as well as the propagation time tT for the overall sheet thickness dT, in setting a first gate B1 for the signal of the first rear wall echo that starts at the moment in time t1S=tE+tMin−tSA and ends at the moment in time t1T=tE+tT+tSE, with tSA and tSE being small safety allowances, in determining an $n^{th}$ gate for the $n^{th}$ rear wall echo that begins at the moment in time tnS=TE+n*tMin−tSA and ends at the moment in time tnT=tE+n*tT+tSE, and in coupling the probe in different ways, more specifically with regard to its emission angle and/or emission site and in thereby aiming at achieving a sufficiently large amplitude of the signal of the first rear wall echo within the first gate and preferably of the signal of the $n^{th}$ rear wall echo within the $n^{th}$ gate as well and in using, more specifically in storing, the achieved maximum for evaluation.

In this method, a worker skilled in the art, more specifically a welding engineer, first dictates the minimum thickness dMin the spot welding joint is intended to have. During spot welding, the electrodes on either side of the sheet connection are pressed to a certain extent into the respective one of the metal sheets, which results in a reduced wall thickness of the spot welding joint. Depending on the shape of the electrodes, which in most cases are spherical or partially spherical, the impressions made by the electrodes are also rounded. The impressions on either side of the sheet connection may be different, and may more specifically have different depths. Generally, the deepest sites of the two impressions are located directly opposite, but they may also be slightly offset. The wall thickness is smallest at the deepest point of the impressions.

The thickness should not be less than the minimum thickness dMin since in such a case there is a risk that the metal sheets be too much weakened mechanically in the region of the spot welding joint. In an advantageous improved implementation, a maximum thickness dMax is also established, it is generally close to the overall sheet thickness. It is desirable that the value for the overall sheet thickness be slightly higher than the value for the maximum thickness, which shows that welding has actually taken place.

The temporal threshold values for gates are now fixed as a function of the values for minimum thickness and overall sheet thickness determined for the configured type of spot welding joint. A first gate is set for the first rear wall echo and in any case another gate for another rear wall echo, more specifically for the second rear wall echo. Three gates are preferably set, more specifically for the first, the second and the third rear wall echo. The starting time and the end time for the respective one of the metal sheets are a result of the time at which the entrance echo occurs with respect to the minimum propagation time and the propagation time for the overall sheet thickness respectively. An allowance, which will be termed safety allowance, is also provided for. Ultrasound testing may now be carried out. If it is performed by hand, a display appears on a monitor. Thereon, the time axis t is plotted down the side of a diagram whereas the voltage values having the amplified echo signals are plotted on the horizontal axis.

If a logarithmic amplifier is being used, the respective ones of the entrance echo and of the subsequent rear wall echo signals can be fully represented. Generally, a linear amplifier is being used, though. The amplification range thereof is adjusted in such a manner that the usually to be expected first rear wall echoes substantially completely fill the monitor without extending beyond it, though. It is thereby assumed that the output voltage swing of the amplifier corresponds to 100% of the monitor height. With such an adjustment, the electrical signal of the entrance echo extends far beyond the top edge of the monitor and is not represented as a result thereof. In contrast to the logarithmic amplifier, it is now difficult to find the peak of the entrance signal. There are different possibilities to determine in this case as well the time at which the entrance echo tE occurs as the center of the sites at which the upward slope and the downward slope reach the top edge of the monitor. Generally, such type approaches are still not precise enough and are suited for approximation. Precise determination is achieved by back calculation. The interval between successive rear wall echoes represents the actual propagation time ta. If one calculates them back from the first entrance echo, one obtains the actual moment in time of the entrance echo tE.

If the inspection procedure is automatized, a monitor is optional. The maximum values of the echo signals are searched within the gates and, as a function thereof, the probe is automatically moved until the amplitudes achieved are sufficiently large. The procedure is the same with manual testing.

If the echo signal present in each gate is large enough, the selected adjustment is good enough and the echo signal sequence can be processed further, more specifically digitized and stored.

In an improved embodiment, it is suggested to also display within the gate the moments in time that correspond to the minimum propagation time and to the maximum propagation time and/or to the propagation time for the overall sheet thickness.

A preferred improvement is achieved by a method by which amplitude threshold values for the gates of the rear wall echoes are set as follows:
 upper threshold value of the echo signal voltage of the first rear wall echo U1Max=100%,
 lower threshold value of the echo signal voltage of the first rear wall echo U1Min=70–90%, preferably 80%;
 upper threshold value of the echo signal voltage of the second rear wall echo U2Max=90–100%, preferably 98%,
 lower threshold value of the echo signal voltage of the second rear wall echo U2Min=20–60%, preferably 40%;
 upper threshold value of the echo signal voltage of the third rear wall echo U3Max=80–100%, preferably 90% and
 lower threshold value of the echo signal voltage of the third rear wall echo U3Min=10–30%, preferably 20%.

Generally, the rear wall echoes decay with increasing order, which is called a decaying sequence of echoes. However, in particular cases, the second rear wall echo is for example larger than the first one. A decaying sequence of echoes is due to the fact that the sound pulse becomes weaker as it travels back and forth with fading in the metal sheets as they are used herein amounting to about 6 dB/mm.

If one does not set all of the gates for the rear wall echoes on the same upper amplitude threshold value, it is easier to differentiate the gates displayed on the monitor. The lower amplitude threshold values of the individual gates are set in such a manner that the echoes at hand are still good enough for further processing.

In a preferred improvement of the method, the graphically represented gates and the rear wall echoes of the same order are each represented specifically and differently from each other on the monitor, for example in a dotted line, a dash-dot line, in undulated lines, and so on. This permits to enhance association.

For the propagation time tT, the maximum propagation time tMax for the overall sheet thickness may be assessed.

In a particularly preferred embodiment, the gate for an nth rear wall echo and the associated signals of the nth rear wall echo are represented graphically on the monitor in another manner than the other rear wall echoes e.g., in a dashed line, a dotted line, a dash-dot line and so on. This allows for good association during manual testing.

Figure 4:
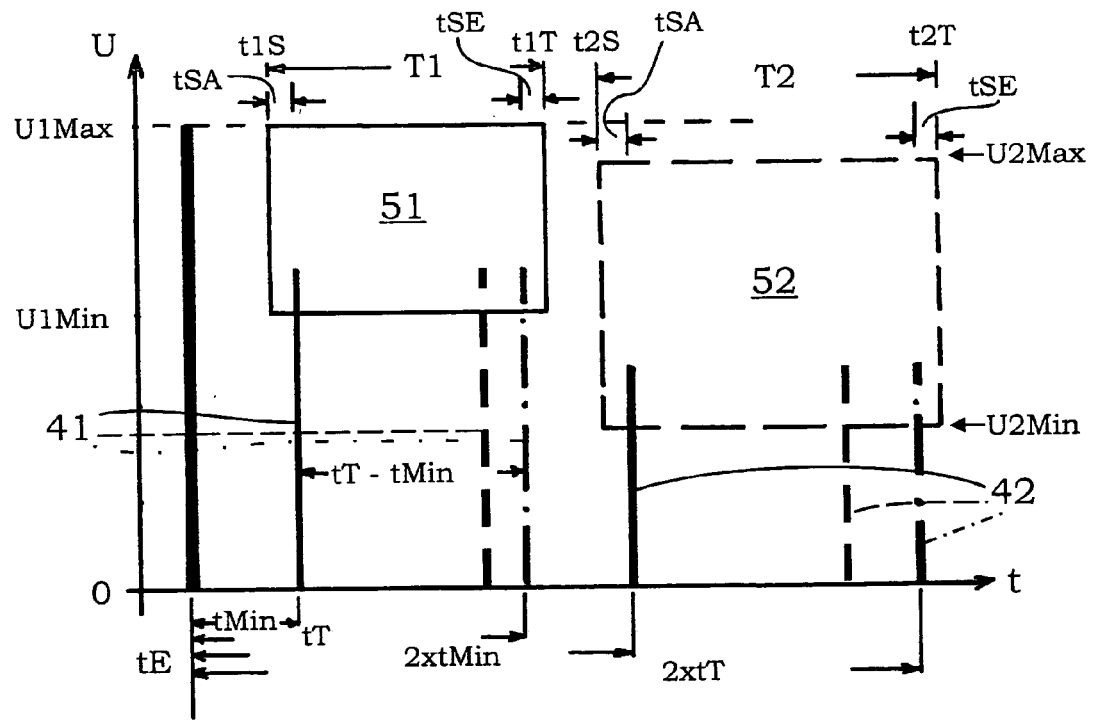
Figure 2:
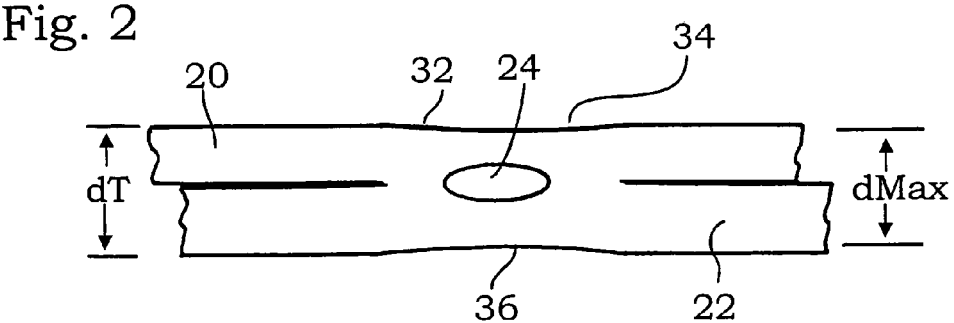
Figure 3:
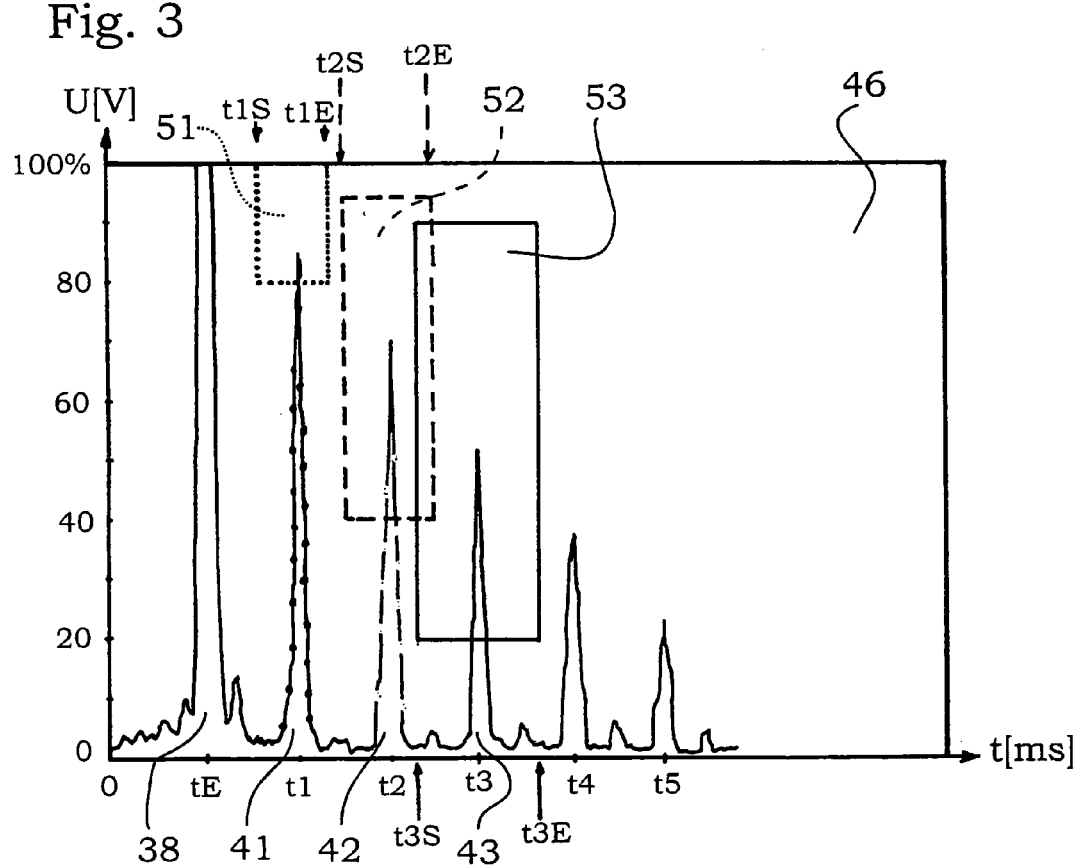

Exemplary embodiments of the invention will be explained and described in closer detail herein after with reference to the drawing. These exemplary embodiments are not meant to limit the scope of the invention. In the drawing:

FIG. 1: shows a schematic side view of a spot welding joint between two metal sheets with maximum electrode impression on both metal sheets and further with different couplings being shown symbolically, FIG. 2: an illustration like FIG. 1, but now in the case of minimum electrode impressions, FIG. 3: a typical monitor picture as a so-called A-picture for the echo signals of a tested spot welding joint and FIG. 4: an illustration similar to FIG. 3, but now shown schematically in order to explain the positioning of the gates.

DETAILED DESCRIPTION OF THE INVENTION

The FIGS. 1 and 2 each show two metal sheets 20, 22, that are joined together by a spot welding joint. This joint is shown symbolically by a welding spot 24. Usually, the metal sheets 20, 22 have a thickness in the mm range, for example between 0.6 and 1.2 mm. A typical application is in the automotive industry. The spot welding joints have each been made, at least as far as practicable, under the same conditions, namely with comparable or identical metal sheets 20, 22, comparable welding processes, and so on. The welding joints constitute a selected type.

If another type of spot welding joints is to be tested, for example other sheet thicknesses and so on, it is possible to use the same process as described herein after but it is generally necessary to set other gate values and so on.

The exemplary embodiments show the connection between two metal sheets 20, 22 although more than two sheets may be joined together. The overall thickness of the sheets joined together is dT. During welding, the spherical electrodes (not shown since well known) are pressed into the surface. FIG. 1 shows the case in which the sheet has the smallest thickness, the so-called minimum thickness dMin, FIG. 1 the case of maximum thickness dMax.

By means of a probe 26, which is only denoted schematically herein since it is well known, an ultrasonic pulse is emitted into the spot welding joint to be tested. Three different main beams 28, 29, 30 corresponding to different orientations and positions of the probe 26 are illustrated. It can be seen that different emissions will result in different responses. The probe 26 is excited through a transmitter 31 and is connected to a receiver 33 in which there is located an amplifier 35. A monitor 46 is mounted downstream thereof.

A PVDF resonator of 4 mm in diameter and with a frequency of 20 MHz is used for example. Coupling occurs through a preliminary water stretch and through a thin membrane that contacts a sheet in the region of the impression 32 made in a known manner by a welding electrode. In the region of the welding spot 24, the diameter of the ultrasonic beams is e.g., about 2 mm at minus 18 dB. The diameter of the sound beam is generally smaller than the diameter of the impression 32 or of the dimension of the welding spot 24 respectively.

The invention finds a coupling that is good enough, meaning it finds within the range of possible positions and orientations as they are denoted by the different main beams 28, 29, 30, a coupling that results in an evaluatable sequence of echoes as it is shown for example in FIG. 3.

FIG. 3 shows a typical picture as it appears during manual testing on a monitor of an ultrasonic testing apparatus with linear amplifier. Any origin may be selected for the time axis, it should be before the time of the entrance echo tE so that this moment in time may still be sufficiently registered. The entrance echo, meaning the direct reflection of a main beam 28, 29, 30 at the front surface 34, has an amplitude clearly in excess of 100%. Amplification of the echo signals is adjusted in such a manner that, within the range of representation, a first rear wall echo 40 comes in close range to 100%, meaning delivers the largest possible signal.

The value 100%, meaning the specially adjusted amplification for testing the spot welding joints of the selected type, is derived using an experimental value that can be obtained in different manners. For example by testing some spot welding joints and by noting the amplification needed for every single one of them, so that the first rear wall echo displayed is sufficiently large. The experimental value thus obtained is used to test all of the other spot welding joints of the same type.

The first rear wall echo occurs at the moment in time t1. Further rear wall echoes are also shown, which occur at the moments in time t2, t3, t4 and t5. Each numeral designates the rank order of the respective one of the rear wall echoes. It can be seen that the echo sequence is what is termed a decaying sequence of echoes. The difference between successive echo signals is the actual sound propagation time ta.

In practical testing, the probe 26 is moved and tilted until the echo sequence obtained is sufficiently good, meaning until the amplitudes U for the rear wall echoes are good enough. In order to provide definable conditions, gates are set. FIG. 3 shows the case of three gates, namely a first gate 51 for the first rear wall echo 41, a second gate 52 for the second rear wall echo 42 and a third gate 53 for the third rear wall echo 43. The gates are also called expected signal values or windows. They constitute selected areas of the monitor 46 the testing operator should particularly heed. The same applies for the automated testing.

The gates 51, 52, 53 are respectively limited by temporal threshold values in the direction of the time axis t and by amplitude threshold values in the direction of the y-axis on which there is plotted the signal voltage U. These limits have already been discussed in detail herein above. In the concrete case of FIG. 3, the first gate 51 is limited by the time values t1S and t1T. With regard to amplitude, the first gate 51 is limited by an upper limit U1Max at 100% and by a lower limit U1Min at 80%.

The second gate 52 is slightly wider in the direction of the time axis because the difference in propagation time between the propagation time of the overall sheet thickness and the minimum propagation time has now to be taken into consideration twice. With respect to time, the gate starts at t2S and ends at t2T. With respect to amplitude, it extends from U2Max=90% down to U2Min=40%.

The third gate 53 is still a little wider, it starts at t3S and ends at t3T. With respect to amplitude it extends from U3Max=80% to U3Min=20%.

As shown in FIG. 3, the gates and the associated rear wall echoes are marked using particular measures, for example by a dotted line for the first gate and by a dashed line for the second gate.

FIG. 4 shows the connections. Now, the rear wall echoes 41–43 are merely shown in dashes. In the gate 51 there is shown the first rear wall echo 41 for the case of minimum thickness of the spot welding joint in solid line, for the case of maximum thickness in a dashed line and for the overall sheet thickness dT in a dash-dot line. The normal cases should be located within these limits. Like all the other gates, the first gate 51 is still slightly larger in the temporal direction, and is continued namely at the beginning by the safety allowance tSA and at the end by the safety allowance tSE.

The same applies to the gate 52 for the second rear wall echo shown, with the alternatives that the solid line corresponds to the minimum thickness of the spot welding joint, the dashed line to the maximum thickness and the dash-dot line to the overall sheet thickness. The safety allowances are the same for all of the gates.

The echoes for the maximum thickness dMax, which are shown in dashed line, occur at the following moments in time: first rear wall echo 41 at the moment in time tE+tMax, second rear wall echo 42 at the moment in time tE+2*tMax. The first gate 51 extends over the total time T1=t1T−t1S. The temporal length of the second gate is T2=t2T−t2S.

The invention claimed is:

1. A method for determining threshold values of gates for permitting to evaluate a good sound coupling during ultrasound testing of a series of spot welding joints of a selected type, said spot welding joints being configured between at least one first metal sheet and at least one second metal sheet, the first sheet having a first sheet thickness and the second metal sheet having a second sheet thickness, the method comprising:
  a) establishing a geometrical minimum thickness dMin for the spot welding joint, said minimum thickness being smaller than an overall sheet thickness dT of the metal sheets joined together with the spot welding joint,
  b) coupling an ultrasonic probe to a spot welding joint to be tested, emitting at least one ultrasound pulse onto a front surface of the spot welding joint and receiving echo signals, the echo signals received comprising at least one entrance echo on the front surface received at a time tT, one echo of a first reflection on a rear wall of the spot welding joint (first rear wall echo) and at least one further ($n^{th}$) rear wall echo,
  c) defining a propagation time tMin of the ultrasound pulse for a path from the front surface to the rear wall and back to the front surface at the minimum thickness dMin as well as the propagation time tT for the overall sheet thickness dT,
  d) setting a first gate B1 for the signal of the first rear wall echo that starts at a time t1S=tE+tMin−tSA and ends at a time t1T=tE+tT+tSE, with tSA and tSE being small safety allowances, e) fixing an $n^{th}$ gate for the $n^{th}$ rear wall echo that begins at a time tnS=tE+n*tMin−tSA and ends at a time tnT=tE+n*tT+tSE, and f) coupling the probe in different ways, whereby at least an emission angle and/or emission site of the probe is modified thereby achieving a sufficiently large amplitude of either the signal of the first rear wall echo within the first gate or the signal of the $n^{th}$ rear wall echo within the $n^{th}$ gate and the achieved maximum is used, and stored, for evaluation.

2. The method in accordance with claim 1, wherein the echo signals are represented on a monitor on an x-axis of which is plotted time t and on a y-axis of which is plotted electrical echo signal U.

3. The method in accordance with claim 2, wherein the safety allowances are assessed as follows:
a) safety allowance at a beginning of the gate tSA is determined to be 10–60% of a difference between the sound propagation time tT for the overall sheet thickness dT and the minimum propagation time tMin and
b) safety allowance at an end of the gate tSE is set as 10–60% of a difference between the sound propagation time for the overall sheet thickness dT and the maximum propagation time tMax.

4. The method in accordance with claim 2, wherein safety allowances are assessed as follows:
a) safety allowance at a beginning of the gate tSA is determined to be 50% of a difference between the sound propagation time tT for the overall sheet thickness dT and the minimum propagation time tMin and
b) safety allowance at an end of the gate tSE is set as 50% of the difference between the sound propagation time for the overall sheet thickness dT and the maximum propagation time tMax.

5. The method in accordance with claim 1, wherein the electrical echo signals received are substantially linearly amplified, an experimental value for an amplitude of the echo signal of the first rear wall echo is determined, and amplification occurs in such a manner that the experimental value lies within an amplification range of an amplifier and has a value as high as possible but below a maximum output voltage of the amplifier.

6. The method in accordance with claim 5, wherein the amplifier has an amplification range of from 0 to 100%, and wherein amplitude threshold values for the gates of the rear wall echoes are set as follows:
upper threshold value of the echo signal voltage of the first rear wall echo U1Max=100%,
lower threshold value of the echo signal voltage of the first rear wall echo U1Min=70–90%,
upper threshold value of the echo signal voltage of a second rear wall echo U2Max=90–100%,
lower threshold value of the echo signal voltage of the second rear wall echo U2Min=20–60%,
upper threshold value of the echo signal voltage of a third rear wall echo U3Max=80–100%,
lower threshold value of the echo signal voltage of the third rear wall echo U3Min=10–30%.

7. The method in accordance with claim 5, wherein the experimental value for the amplitude of the echo signal of the first rear wall echo is determined by testing a greater number of spot welding joints.

8. The method in accordance with claim 5, wherein the amplifier has an amplification range of 0 to 100%, and wherein amplitude threshold values for the gates of the rear wall echoes are set as follows:
upper threshold value of the echo signal voltage of the first rear wall echo U1Max=100%,
lower threshold value of the echo signal voltage of the first rear wall echo U1Min=80%;
upper threshold value of the echo signal voltage of a second rear wall echo U2Max=98%,
lower threshold value of the echo signal voltage of the second rear wall echo U2Min=40%;
upper threshold value of the echo signal voltage of a third rear wall echo U3Max=90% and
lower threshold value of the echo signal voltage of the third rear wall echo U3Min=20%.

9. The method in accordance with claim 1, wherein one of two or three gates are set.

10. The method in accordance with claim 1, wherein the gates for the $n^{th}$ rear wall echo and associated signals of the $n^{th}$ rear wall echo are represented graphically on a monitor in another manner than other rear wall echoes.

11. The method in accordance with claim 1, wherein a maximum thickness dMax for the spot welding joint is also established.

12. The method in accordance with claim 11, wherein time tE of the entrance echo is determined as follows:
a) a time of a maximum of the first rear wall echo t1 is established and a mean value of a maximum propagation time tMax and a minimum propagation time tMin is subtracted therefrom, the result obtained being called tEa,
b) a time of a maximum of the second rear wall echo t2 is determined and a double value of the mean value of maximum propagation time tMax and minimum propagation time tMin is subtracted therefrom, the result obtained being called tEb, and
c) a mean value of tEa and tEb is assessed as tE, which is the time of the entrance echo.

13. The method in accordance with claim 1, wherein the wall thickness of the first and second sheets is less than 12 mm.

14. The method in accordance with claim 1, wherein the gates for the $n^{th}$ rear wall echo and the associated signals of the nth rear wall echo are represented graphically on a monitor as at least one of a dashed line, a dotted line, and a dash-dot line.

15. The method in accordance with claim 1, wherein the wall thickness of the sheets is less than 2 mm.

16. The method in accordance with claim 1, wherein the wall thickness of the sheets is less than 1.2 mm.

* * * * *